United States Patent [19]

Thigpen

[11] Patent Number: 5,690,793

[45] Date of Patent: Nov. 25, 1997

[54] PURIFICATION PROCESS FOR CYCLIC FORMALS

[75] Inventor: Hubert H. Thigpen, Corpus Christi, Tex.

[73] Assignee: Hoechst Celanese Corporation, Warren, N.J.

[21] Appl. No.: 509,793

[22] Filed: Aug. 1, 1995

Related U.S. Application Data

[63] Continuation of Ser. No. 180,173, Jan. 11, 1994, abandoned.

[51] Int. Cl.$^6$ .......................... B01D 3/34; C07D 317/12
[52] U.S. Cl. .................. 203/17; 203/63; 203/64; 549/430
[58] Field of Search .................. 203/14, 17, 64, 203/81, 63, 430; 549/377

[56] References Cited

U.S. PATENT DOCUMENTS

| | | | |
|---|---|---|---|
| 2,350,940 | 6/1944 | Squires | 549/430 |
| 3,857,759 | 12/1974 | Fiore et al. | 203/14 |
| 4,007,095 | 2/1977 | Wolf et al. | 203/64 |
| 4,229,262 | 10/1980 | Reed et al. | 203/64 |
| 4,764,626 | 8/1988 | Heuvelsland | 549/377 |

OTHER PUBLICATIONS

CA 118: 126957 Abstract.

*Primary Examiner*—Virgania Manoharan
*Attorney, Agent, or Firm*—James M. Hunter, Jr.

[57] ABSTRACT

A purification process for cyclic formals, in which water is efficiently removed from a crude cyclic formal, namely, a mixture of a cyclic formal and water which is difficult to be separated from the mixture, thereby obtaining a cyclic formal of high purity which contains only extremely small amounts of water and impurities.

The purification process for cyclic formals is characterized by the steps of supplying a mixture of a cyclic formal and water into a distillation tower, effecting distillation while supplying a hydrophilic solver (A) having a boiling point from 180° to 250° C. and a purified cyclic formal (X) containing not more than 200 ppm of water into the distillation tower at positions higher than the supply position of the mixture and higher than the supply position of the hydrophilic solvent (A), respectively, and taking out a purified cyclic formal from the top of the tower as a distillate.

9 Claims, 2 Drawing Sheets

PURIFICATION PROCESS FOR CYCLIC FORMALS

This is a continuation of application Ser. No. 08/180,173 filed on Jan. 11, 1994, now abandoned.

BACKGROUND OF THE INVENTION

1. Field of the Invention

The present invention relates to a purification process for cyclic formals which are useful as solvents, intermediates of drugs, starting materials for resins, and the like. More particularly, it relates to an economically advantageous purification process for obtaining cyclic formals of high purity which contains only very small amounts of water and other impurities, in which water is efficiently removed from a mixture of a cyclic formal and water which is difficult to be separated from the mixture because of the azeotropy between cyclic formal and water.

2. Description of Related Art

Cyclic formals typified by 1,3-dioxolan, 1,4-butanediol formal, diethylene glycol formal, 4-methyl-1,3-dioxolan, 1,3-dioxane, 1,3,6-trioxolane, etc. are known to be obtainable from cyclizing reactions between a corresponding glycol and an aldehyde, and between a corresponding alkylene oxide and an aldehyde. For example, concerning a method for preparing a typical cyclic formal, 1,3-dioxolan, German patent No. 1914209 discloses a process for preparing it by reacting glycol with formaldehyde in the presence of an acid catalyst, and Ind. Eng. Chem., 46,787 (1954) and U.S. Pat. No. 3,857,759 both disclose a process for preparing 1,3-dioxolan by reacting glycol and paraformaldehyde in the presence of an acid catalyst.

These processes for preparing cyclic formals which employ a glycol and an aldehyde as starting materials involve drawbacks in that the cyclic formal produced and a by-produced water or water which is present in a form of an aqueous aldehyde solution often co-boil (azeotropy), thereby rendering separation of water difficult by ordinary distillation steps.

Taking 1,3-dioxolan as an example, the above mentioned German patent No. 1914209 describes that as much as 7% of water is contained. In order to obtain 1,3-dioxolan of high purity by removing water from a mixture of 1,3-dioxolan and water, the above-mentioned Ind. Eng. Chem., 46,787 (1954) discloses a process in which a reaction distillate containing 1,3-dioxolan and water is added with sodium chloride for phase separation into two phases, and the organic phase is subjected to a further distillation for purification, while U.S. Pat. No. 3,857,759 discloses a process in which a reaction distillate is added with cyclohexane before purification. However, the former is not suitable as an industrial purification process, and the latter raises a problem in that water cannot be separated sufficiently for obtaining 1,3-dioxolan of high purity.

These phenomena do not specifically occur only in processes for preparing 1,3-dioxolan, but are common in processes for obtaining cyclic formals which form an azeotropic system with water. Accordingly, an economical purification process for obtaining cyclic formals of high purity in which water is efficiently removed from a mixture of a cyclic formal and water has still been desired.

Under the above circumstances, the present inventors have carried out extensive studies in order to solve the aforementioned problems. Having started from the use of extraction distillation, they have conducted researches as to which solvents should be used, at which position the solvent should be supplied to the distillation tower, and how the solvent can be prevented from migrating and contaminating purified cyclic formals, leading to completion of the present invention.

SUMMARY OF THE INVENTION

Accordingly, an object of the present invention is to provide a purification process for a cyclic formal which comprises the steps of supplying a mixture of a cyclic formal and water into a distillation tower at a supply position, effecting distillation while supplying a hydrophilic solvent (A) having a boiling point from 180° to 250° C. and a purified cyclic formal (X) containing not more than 200 ppm of water into the distillation tower at positions higher than the supply position of the mixture and higher than the supply position of the hydrophilic solvent (A), respectively, and taking out a purified cyclic formal as a distillate from the top of the tower.

Another object of the present invention is to provide a purification process for a cyclic formal as described above, wherein the hydrophilic solvent (A) is a polyol, a dimer thereof, or a monoalkylether of a polyol or the dimer.

Another object of the present invention is to provide a purification process for a cyclic formal as described above, wherein the hydrophilic solvent (A) is selected from the group consisting of 1,4-butanediol, diethylene glycol, 1,2-propanediol, 1,3-propanediol, dipropylene glycol and monomethyl ethers thereof.

Another object of the invention is to provide a purification process for a cyclic formal as described above, wherein the distillation tower is a plate distillation tower, and the position at which the hydrophilic solvent (A) is supplied is a position between the second to twentieth plates counted from the top plate, and the position at which the purified cyclic formal (X) is supplied is a position between the top to fifteenth plates counted from the top plate.

Another object of the invention is to provide a purification process for a cyclic formal as described above, wherein the distillation tower is a packed distillation tower, and the position at which the hydrophilic solvent (A) is supplied is the position of a theoretical plate having a number between 0.5 to 10 counted from the theoretical top plate of the packed distillation tower, and the position at which the purified cyclic formal (X) is supplied is the position of a theoretical plate between the top plate and the seventh theoretical plate counted from the theoretical top plate of the packed distillation tower.

Another object of the invention is to provide a purification process for a cyclic formal as described above, wherein the quantity of the hydrophilic solvent (A) supplied is from 1 to 15 times, on a molar basis, the quantity of water in the mixture of cyclic formal and water.

Another object of the invention is to provide a purification process for a cyclic formal as described above, wherein a pre-concentrated mixture which contains a cyclic formal having a concentration more than 80% by weight up to a concentration which forms an azeotrope is supplied to the tower.

Another object of the invention is to provide a purification process for a cyclic formal as described above, wherein the quantity of the purified cyclic formal (X) supplied is from 10 to 100% by weight based on the quantity of the hydrophilic solvent (A) supplied.

Another object of the invention is to provide a purification process for a cyclic formal as described above, wherein the cyclic formal contained in the mixture and the cyclic formal of the purified cyclic formal (X) are both 1,3-dioxolan.

The above and other objects, features and advantages of the present invention will become apparent from the following description.

DETAILED DESCRIPTION OF THE INVENTION AND PREFERRED EMBODIMENTS

The present invention is directed to a purification process of cyclic formals, and specific examples of the cyclic formals to which the present invention is applicable include 1,3-dioxolan, 1,4-butanediol formal, diethylene glycol formal, 4-methyl-1,3-dioxolan and 1,3-dioxane, with 1,3-dioxolan being preferable. Moreover, it is preferable that the cyclic formal contained in the mixture and the cyclic formal of the purified cyclic formal (X) are identical.

Figure 1:
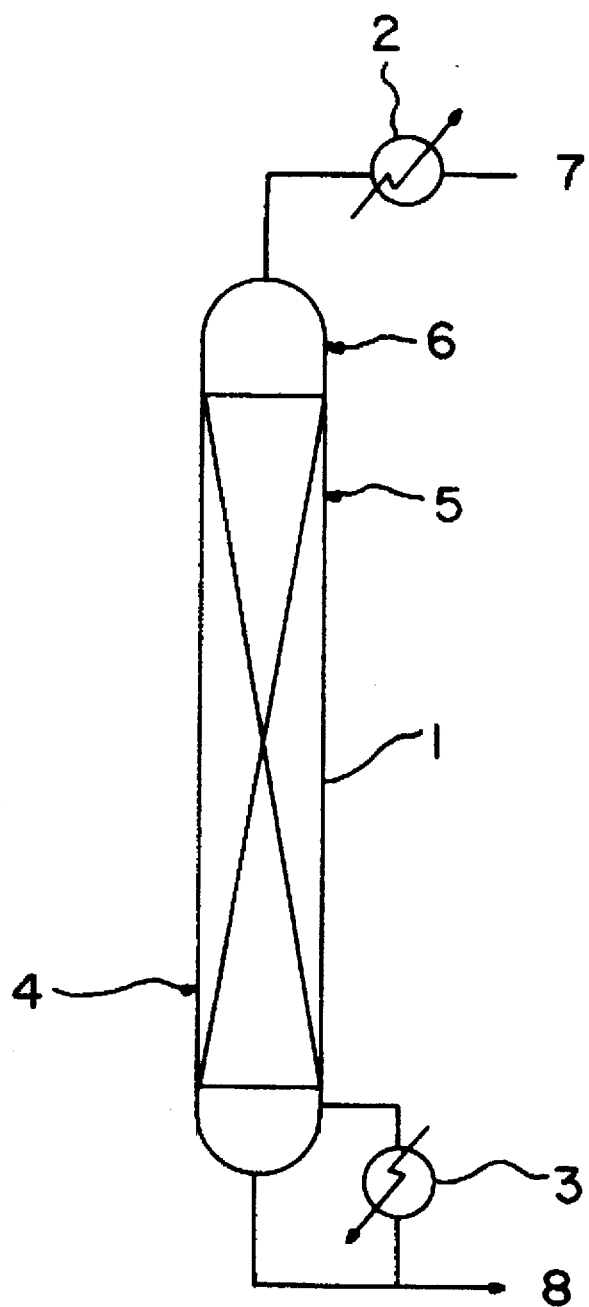
FIG. 1 is a schematic diagram showing a conceptional example of the distillation system used for performing the purification process for cyclic formals according to the present invention.

The present invention will now be described with reference to the distillation system shown in FIG. 1. In FIG. 1, numeral 1 indicates a distillation tower, numeral 2 indicates a condenser, numeral 3, indicates a reboiler, numeral 4 indicates a supply position of a mixture containing a cyclic formal and water, numeral 5 indicates a supply position of a hydrophilic solvent (A), numeral 6 indicates a supply position of a purified cyclic formal (X), numeral 7 indicates a distillate at the top (may be referred to as a top distillate) which is a purified cyclic formal, and numeral 8 indicates a bottom waste. As described hereinbefore, purification of cyclic formals involves a limitation, that is, they cannot be purified beyond the azeotropic composition of a cyclic formal and water by ordinary distillation procedures. However, according to the present invention, supply of a hydrophilic solvent (A) into the distillation tower destroys the azeotropic system formed in ordinary distillations, allowing water and impurities to be removed. Moreover, since a purified cyclic formal (X) is supplied at a position higher than the supply position of the hydrophilic solvent (A), migration of hydrophilic solvent (A) into the top distillate is prevented, and surprisingly enough, amount of contaminating water in the top distillate is further reduced, yielding highly purified cyclic formals at the top of the tower. Such effects cannot be obtained in ordinary distillation procedures where part of the top distillate, a cyclic formal, is returned to the tower and is refluxed in place of a purified cyclic formal (X). Water contained in the starting mixture, part of a cyclic formal, hydrophilic solvent (A), and impurities such as formaldehyde and reaction byproducts are taken out as a bottom waste from the bottom of the tower.

The hydrophilic solvents (A) used in the present invention are preferably those which are miscible with water in arbitrary proportions at ordinary temperatures, and have a boiling point from 180° to 250° C., preferably from 190° to 250° C. Examples of the hydrophilic solvents (A) include polyols, dimers of polyols, and monoalkylethers of polyols and the dimers. Preferable alkyl groups of the monoalkylethers are those having 1 to 4 carbon atoms, among which methyl and ethyl are more preferred, with methyl being particularly preferred. Specific examples of the hydrophilic solvents (A) include 1,4-butanediol, diethylene glycol, 1,2-propanediol, 1,3-propanediol, dipropylene glycol, ethylene glycol and monomethyl ethers thereof. These hydrophilic solvents (A) are used singly or in arbitrary combination of two or more. Among the species of hydrophilic solvents (A), 1,4-butanediol, diethylene glycol, 1,2-propanediol are preferred.

The amount of hydrophilic solvent (A) to supply is not particularly limited. It is generally from 1 to 15 times, particularly preferably from 1.5 to 10 times, in a molar ratio, the quantity of water contained in the mixture of cyclic formal and water.

In cases where the water content in the mixture supplied to the distillation tower at the position 4 is high, and a highly purified cyclic formal is desired, abundant hydrophilic solvent (A) is required, which leads to the requirement of a large amount of purified cyclic formal (X). Therefore, according to the present invention, it is preferred that the mixture to be supplied at position 4 be properly dehydrated in advance by ordinary distillation procedures or the like so as to raise the concentration of cyclic formal not less than 80% by weight, or even higher concentrations close to the azeotrope.

In the purification process according to the present invention, the position at which the hydrophilic solvent (A) is supplied to the distillation tower is any position higher than the supply position of the mixture of cyclic formal and water. It is preferred that the distance between the two positions be as long as possible. However, in order to prevent the hydrophilic solvent (A) from migrating into the top distillate, which is purified cyclic formal 7, the supply position is preferably lower than the second plate (plate No. 2), more preferably between the second (No. 2) to twentieth (No. 20) plates counted from the top plate when the distillation tower is a plate distillation tower. This sufficiently prevents hydrophilic solvent (A) from migrating into the purified cyclic formal and contaminating it, and also suppresses the water content in the purified cyclic formal 7 at a low level. Similarly, when the distillation tower is a packed distillation tower, the position at which the hydrophilic solvent (A) is supplied is preferably lower than 0.5 in terms of a theoretical plate number counted from the top of the tower, more preferably between 0.5 to 10 (theoretical plate Nos.). In this connection, the supply position of the mixture may be at any positions of plates, packed portion, or bottom of the tower as long as the above conditions are met.

According to the present invention, a purified cyclic formal (X) is further supplied to the distillation tower at a position higher than the supply position of the hydrophilic solvent (A). The purified cyclic formal (X) to be used in the present invention is such that the top distillate of the distillation tower 1, namely, a distilled cyclic formal is further purified by distillation, adsorption or the like so as to have the water content of not more than 200 ppm, preferably not more than 150 ppm, more preferably not more than 100 ppm. By supplying a purified cyclic formal (X) at the specific positions as described above, hydrophilic solvent (A) can be effectively prevented from migrating into distillate 7 taken out from the top and contaminating it, and moreover, amount of contaminating water in the top distillate is further reduced. The supply position of the purified cyclic formal (X) is preferably between the top (No. 1) plate to 15th plate counted from the top when the distillation tower is a plate distillation tower, and from the theoretical top (No. 1) plate to the 7th plate in terms of the number of theoretical plates counted from the theoretical top plate in case of a packed distillation tower. The optimum amount of the purified cyclic formal (X) to be supplied differs depending on the amount of the hydrophilic solvent (A) supplied and also on the relationship between the supply positions of the cyclic formal (X) and hydrophilic solvent (A). It is generally from 10 to 100% by weight, preferably from 15 to 80% by weight based on the amount of the hydrophilic solvent (A) supplied. In the practice of the present invention, the purification operation of cyclic formals can be performed while refluxing as in ordinary distillation processes.

No particular limitation is imposed on the types of distillation tower useful for purifying cyclic formals according to the present invention. In cases where plate distillation towers are used, any known types are usable including bubble cap tray, uniflux tray, bulb tray, Natter bulb tray, ballast tray, sieve tray, Venturi tray, Kittel tray, turbo grid tray, ripple tray and the like.

The distillation tower may be a packed distillation tower. Any types of packing materials are usable including those of ring types such as Raschig rings, Lessing rings, divided rings and pole rings; saddle types such as bar saddles and interlock saddles; and other types such as Goodroigh packings, Stedman packings, Dickson rings, McMahon packings, helix packings, teralet, cross-spiral packings and so on.

According to the purification process of the present invention, even when the mixture of cyclic formal and water to be supplied to the distillation tower contains unreacted formaldehyde or reaction byproducts, most of them can be satisfactorily removed. Moreover, although the purified cyclic formal obtained as a top distillate according to the present invention is very pure, it may further be subjected to another distillation or adsorption steps if necessary. In particular, it is preferred that the purified cyclic formal (X) to be used in the present invention be one which has undergone such a further purification. The purification process of the present invention is very useful for purifying 1,3-dioxolan.

EXAMPLES

The present invention will further be described by way of examples, which however, should not be construed as limiting the invention thereto.

Examples 1 to 3

Figure 2:
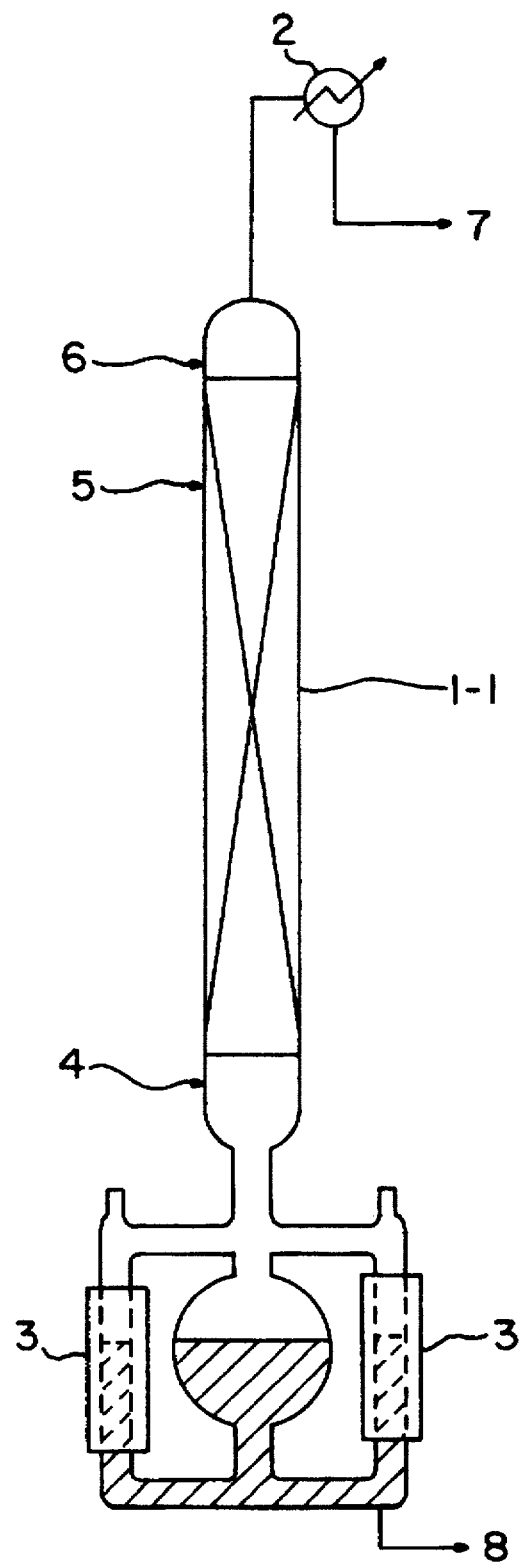
FIG. 2 is a schematic diagram showing the distillation system used in Examples according to the present invention and in Comparative Examples.

Distillation was performed using a distillation system shown in FIG. 2. A plate distillation tower 1-1 (diameter of the tower=50 mm, 50 plates, sieve tray) was fed with a mixture containing 93% by weight of 1,3-dioxolan and 7% by weight of water at the bottom of the tower 1-1 at a flow rate shown in Table 1, while a hydrophilic solvent (A) shown in Table 1 was fed at the tenth plate from the top at the flow rate shown in Table 1, and 1,3-dioxolan containing 130 ppm of water (purified 1,3-dioxolan (X)) was fed at the top plate at a flow rate shown in Table 1. The flow rates of distillate 7 from the top and waste 8 from the bottom under the steady conditions are also shown in Table 1. The compositions of the top distillates and the bottom wastes under the steady conditions are shown in Table 2. As apparent from Table 2, a very pure 1,3-dioxolan containing extremely small amounts of water and solvent was obtained as a distillate.

The mixture supplied to the tower in this example had a composition close to the azeotrope of 1,3-dioxolan and water, from which ordinary distillation procedures cannot remove water, that is, 1,3-dioxolan can no more be purified by conventional processes.

TABLE 1

|  | Ex. 1 | Ex. 2 | Ex. 3 |
| --- | --- | --- | --- |
| Hydrophilic solvent (A) | BD | DEG | PD |
| Flow rate of mixture supplied (g/hr) | 308 | 386 | 312 |
| Flow rate of hydrophilic solvent (A) supplied (g/hr) | 604 | 583 | 715 |
| Purified 1,3-dioxolan (X) (g/hr) | 118 | 120 | 121 |
| Flow rate of distillate from the top (g/hr) | 304 | 385 | 290 |
| Flow rate of waste from the bottom (g/hr) | 726 | 704 | 858 |

BD: 1,4-butanediol
DEG: diethylene glycol
PD: 1,2-propanediol

TABLE 2

| Hydrophilic solvent (A): | Ex. 1 BD | Ex. 2 DEG | Ex. 3 PD |
| --- | --- | --- | --- |
| Distillate from the top |  |  |  |
| 1,3-Dioxolan (% by weight) | 99.9 | 99.9 | 99.9 |
| Water (ppm) | 250 | 221 | 292 |
| Hydrophilic solvent (A) (ppm) | 5 | 0 | 70 |
| Waste from the bottom |  |  |  |
| 1,3-Dioxolan (% by weight) | 13.8 | 13.2 | 14.2 |
| Water (% by weight) | 3.0 | 3.8 | 2.4 |
| Hydrophilic solvent (A) (% by weight) | 83.2 | 83.0 | 83.4 |

BD: 1,4-butanediol
DEG: diethylene glycol
PD: 1,2-propanediol

Comparative Examples 1 to 3

The procedure of Examples 1 to 3 was followed except that part of the top distillate, 1,3-dioxolan was refluxed in the distillation tower instead that a purified 1,3-dioxolan (X) was supplied to the tower. The amount of reflux was carefully controlled so that it became equal to the amount of the purified 1,3-dioxolan (X) supplied in Examples 1 to 3. The compositions of the top distillates are shown in Table 3.

TABLE 3

| Hydrophilic solvent (A): | Comp. Ex. 1 BD | Comp. Ex. 2 DEG | Comp. Ex. 3 PD |
| --- | --- | --- | --- |
| Distillate from the top |  |  |  |
| 1,3-Dioxolan (% by weight) | 99.9 | 99.9 | 99.8 |
| Water (ppm) | 1300 | 1000 | 1700 |
| Hydrophilic solvent (A) (ppm) | 20 | 15 | 180 |

BD: 1,4-butanediol
DEG: diethylene glycol
PD: 1,2-propanediol

Examples 4 to 6

The procedure of Examples 1 to 3 was followed except that the supply position of the hydrophilic solvent (A) was changed from the top to the second plate. The compositions of the top distillates are shown in Table 4.

TABLE 4

| Hydrophilic solvent (A): | Ex. 4<br>BD | Ex. 5<br>DEG | Ex. 6<br>PD |
|---|---|---|---|
| Distillate from the top | | | |
| 1,3-Dioxolan (% by weight) | 99.9 | 99.9 | 99.9 |
| Water (ppm) | 240 | 215 | 270 |
| Hydrophilic solvent (A) (ppm) | 25 | 15 | 250 |

BD: 1,4-butanediol
DEG: diethylene glycol
PD: 1,2-propanediol

Comparative Examples 4 to 6

The procedure of Examples 4 to 6 was followed except that part of the distillate from the top, namely, part of 1,3-dioxolan taken out from the top was refluxed instead of supplying a purified 1,3-dioxolan (X). The amount of reflux was carefully controlled so that it became possibly equal to the amount of the purified 1,3-dioxolan (X) supplied in Examples 4 to 6. The compositions of the top distillates are shown in Table 5.

TABLE 5

| Hydrophilic solvent (A): | Comp.<br>Ex. 4<br>BD | Comp.<br>Ex. 5<br>DEG | Comp.<br>Ex. 6<br>PD |
|---|---|---|---|
| Distillate from the top | | | |
| 1,3-Dioxolan (% by weight) | 99.9 | 99.9 | 99.8 |
| Water (ppm) | 1200 | 1000 | 1500 |
| Hydrophilic solvent (A) (ppm) | 45 | 30 | 410 |

BD: 1,4-butanediol
DEG: diethylene glycol
PD: 1,2-propanediol

Examples 7 to 9

Distillation was performed using a distillation system shown in FIG. 2. A packed distillation tower 1-1 (diameter of the tower=50 mm, 22 theoretical plates, packed with metallic Raschig rings) was fed with a mixture containing 93% by weight of 1,3-dioxolan and 7% by weight of water at the bottom of the tower 1-1, while a hydrophilic solvent (A) was fed at the second theoretical plate from the top, and 1,3-dioxolan containing 130 ppm of water (purified 1,3-dioxolan (X)) was fed at the top theoretical plate. The flow rates of the three were each controlled to be in agreement with Examples 1 to 3. The compositions of the top distillates under the steady conditions are shown in Table 6. As apparent from Table 6, a very pure 1,3-dioxolan containing extremely small amounts of water and solvent was obtained as a distillate.

TABLE 6

| Hydrophilic solvent (A): | Ex. 7<br>BD | Ex. 8<br>DEG | Ex.9<br>PD |
|---|---|---|---|
| Distillate from the top | | | |
| 1,3-Dioxolan (% by weight) | 99.9 | 99.9 | 99.9 |
| Water (ppm) | 270 | 250 | 310 |
| Hydrophilic solvent (A) (ppm) | 10 | 8 | 110 |

BD: 1,4-butanediol
DEG: diethylene glycol
PD: 1,2-propanediol

Comparative Examples 7 to 9

The procedures of Examples 7 to 9 was followed except that part of the distillate from the top, namely, part of 1,3-dioxolan taken out from the top was refluxed instead of supplying a purified 1,3-dioxolan (X). The amount of reflux was carefully controlled so that it became possibly equal to the amount of the purified 1,3-dioxolan (X) supplied in Examples 7 to 9. The compositions of the top distillates are shown in Table 7.

TABLE 7

| Hydrophilic solvent (A): | Comp.<br>Ex. 7<br>BD | Comp.<br>Ex. 8<br>DEG | Comp.<br>Ex. 9<br>PD |
|---|---|---|---|
| Distillate from the top | | | |
| 1,3-Dioxolan (% by weight) | 99.8 | 99.9 | 99.8 |
| Water (ppm) | 1500 | 1300 | 2100 |
| Hydrophilic solvent (A) (ppm) | 35 | 30 | 380 |

BD: 1,4-butanediol
DEG: diethylene glycol
PD: 1,2-propanediol

As described hereinabove, the present invention provides an economical purification process for crude cyclic formals containing water which was conventionally thought to be difficult to purify because of the azeotropy between the formals and water. The process of the invention yields highly pure cyclic formals on a steady basis, and is very useful and advantageous in the industry.

I claim:

1. A purification process for removing water from cyclic formals which comprises the steps of supplying a mixture of a cyclic formal selected from the group consisting of 1,3-dioxolan, 1,4-butanediol formal, diethylene glycol formal, 4-methyl-1,3-dioxolan and 1,3-dioxane, and water into a distillation tower at a supply position, effecting distillation while supplying a hydrophilic solvent (A) selected from the group consisting of 1,4-butanediol monomethyl ether, diethylene glycol monomethyl ether, 1,2-propanediol monomethyl ether, 1,3-propanediol monomethyl ether and dipropylene glycol monomethyl ether having a boiling point from 180° to 250° C. at a position on the tower higher than the mixture, and supplying a purified cyclic formal (X) containing not more than 200 ppm of water into the distillation tower at a position higher than the supply position of the hydrophilic solvent (A), and taking out a purified cyclic formal as a distillate from the top of the tower, and hydrophilic solvent (A) containing water from the bottom of the tower, wherein supplying the purified cyclic formal (X) into the distillation tower at a position higher than the supply position of the hydrophilic solvent (A) prevents migration of hydrophilic solvent (A) and water into the distillate.

2. The process according to claim 1, wherein the distillation tower is a plate distillation tower, and the position at which the hydrophilic solvent (A) is supplied is a position between the second to twentieth plates counted from the top plate, and the position at which the purified cyclic formal (X) is supplied is a position between the top to fifteenth plates counted from the top plate.

3. The process according to claim 2, wherein the quantity of the hydrophilic solvent (A) supplied is from 1 to 15 times, on a molar basis, the quantity of water in the mixture of cyclic formal and water supplied to the tower.

4. The process according to claim 1, wherein the distillation tower is a packed distillation tower, and the position at which the hydrophilic solvent (A) is supplied is the position of a theoretical plate having a number between 0.5 to 10 counted from the theoretical top plate of the packed distillation tower, and the position at which the purified cyclic formal (X) is supplied is the position of a theoretical plate between the top plate and the seventh theoretical plate counted from the theoretical top plate of the packed distillation tower.

5. The process according to claim 4, wherein the quantity of the hydrophilic solvent (A) supplied is from 1 to 15 times, on a molar basis, the quantity of water in the mixture of cyclic formal and water supplied to the tower.

6. The process according to claim 1, wherein the quantity of the hydrophilic solvent (A) supplied is from 1 to 15 times, on a molar basis, the quantity of water in the mixture of cyclic formal and water supplied to the tower.

7. The process according to claim 1, wherein a pre-concentrated mixture which contains a cyclic formal having a concentration more than 80% by weight up to a concentration which forms an azeotrope of cyclic formal and water is supplied to the tower.

8. The process according to claim 1, wherein the quantity of the purified cyclic formal (X) supplied is from 10 to 100% by weight based on the quantity of the hydrophilic solvent (A) supplied.

9. The process according to claim 1, wherein the cyclic formal contained in the mixture and the cyclic formal of the purified cyclic formal (X) are both 1,3-dioxolan.

* * * * *